United States Patent
Champenois et al.

(10) Patent No.: US 9,989,464 B2
(45) Date of Patent: Jun. 5, 2018

(54) NON-DESTRUCTIVE DETECTION METHOD OF CHARGED PARTICLES WITHOUT MASS LIMITATION

(71) Applicants: CENTRE NATIONAL DE LA RECHERCHE SCIENTIFIQUE (CNRS), Paris (FR); UNIVERSITE D'AIX-MARSEILLE, Marseilles (FR)

(72) Inventors: Caroline Antoinette Madeleine Champenois, Allauch (FR); Laurent Hilico, Maisons-Alfort (FR); Christophe Michel René Jouvet, Marseilles (FR); Jofre Pedregosa Gutierrez, Marseilles (FR); Martina Knoop, Marseilles (FR); Claude Dedonder-Lardeux, Marseilles (FR)

(73) Assignees: CENTRE NATIONAL DE LA RECHERCHE SCIENTIFIQUE (CNRS), Paris (FR); UNIVERSITE D'AIX-MARSEILLE, Marseille (FR)

(*) Notice: Subject to any disclaimer, the term of this patent is extended or adjusted under 35 U.S.C. 154(b) by 0 days. days.

(21) Appl. No.: 15/514,089

(22) PCT Filed: Sep. 25, 2015

(86) PCT No.: PCT/EP2015/072165
§ 371 (c)(1),
(2) Date: Mar. 24, 2017

(87) PCT Pub. No.: WO2016/046396
PCT Pub. Date: Mar. 31, 2016

(65) Prior Publication Data
US 2017/0299514 A1    Oct. 19, 2017

(30) Foreign Application Priority Data
Sep. 26, 2014 (EP) .................. 14306498

(51) Int. Cl.
*G01T 1/10* (2006.01)
*G01N 21/64* (2006.01)

(52) U.S. Cl.
CPC ............... *G01N 21/6402* (2013.01); *G01N 2201/06113* (2013.01)

(58) Field of Classification Search
CPC .......... G01N 21/6428; G01N 21/6458; G01N 21/64; G01N 21/6408; G01N 2021/6421
See application file for complete search history.

(56) References Cited

U.S. PATENT DOCUMENTS

| | | |
|---|---|---|
| 5,591,969 A | 1/1997 | Park et al. |
| 5,770,857 A | 6/1998 | Fuerstenau et al. |
| 2008/0230692 A1 | 9/2008 | Reilly et al. |

OTHER PUBLICATIONS

Willitsch et al. "Chemical applications of laser- and sympathetically-cooled ions in traps", Physical Chemistry Chemical Physics, Oct. 22, 2008, p. 7200-7210.*

(Continued)

*Primary Examiner* — David Porta
*Assistant Examiner* — Mamadou Faye
(74) *Attorney, Agent, or Firm* — Pillsbury Winthrop Shaw Pittman LLP

(57) ABSTRACT

A non-destructive method for detecting charged particles, includes measuring a reference value of at least one physical parameter of an ion cloud confined in an ion trap; performing an injection of a sample in the ion cloud confined in the ion trap, the sample crossing the ion cloud and getting out the ion cloud without being trapped inside the ion trap; measuring a first experimental value of the at least one physical parameter of the ion cloud; and comparing the first experimental value with the reference value in order to determine the presence of at least one charged particle in the sample, or the absence of any charged particle in the sample.

9 Claims, 2 Drawing Sheets

(56) References Cited

OTHER PUBLICATIONS

Wellers et al. "Resonant IR multi-photo dissociation spectroscopy of trapped and sympathetically cooled biomolecular ion species", Physical Chemistry Chemical Physics, 2011, p. 18799-18799.*
International Preliminary Report on Patentability and the Written Opinion of the International Searching Authority as issued in International Patent Application No. PCT/EP2015/072165, dated Mar. 28, 2017.
International Search Report as issued in International Patent Application No. PCT/EP2015/072165, dated Apr. 4, 2016.
Cai, Y., et al., "Optical Detection and Charge-State Analysis of MALDI-Generated Particles with Molecular Masses Larger Than 5 MDa," Analytical Chemistry, vol. 74, No. 17, Sep. 2002, XP055172596, pp. 4434-4440.

* cited by examiner

NON-DESTRUCTIVE DETECTION METHOD OF CHARGED PARTICLES WITHOUT MASS LIMITATION

CROSS-REFERENCE TO RELATED APPLICATIONS

This is the U.S. National Stage of PCT/EP2015/072165, filed Sep. 25, 2015, which in turn claims priority to European Patent Application No. 14306498.8, filed Sep. 26, 2014, the entire contents of all applications are incorporated herein by reference in their entireties.

FIELD

The present invention relates to a non-destructive detection method of charged particles, and more particularly to a non-destructive detection method of charged particles without mass limitation. The present detection method has neither an upper nor a lower limit in mass range. The present detection method allows in particular the detection of charged particles having a mass greater than $10^6$ Da. Said particles may for example be atoms, molecules, clusters, nanoparticles, biomolecules, viruses, DNA, etc. More generally, said particles may be of any type of biological particle.

BACKGROUND

Two main techniques are currently used to detect charged particles, or ions. In the present document, the expression "detecting charged particles" means "determining the presence of at least one charged particle, or the absence of any charged particle".

The first one is based on FTICR ("Fourier Transform Ion Cyclotron Resonance") mass spectrometry. Ions are trapped by a homogeneous static magnetic field of a Penning trap, and excited at their resonant cyclotron frequencies by a spatially inhomogeneous static electric field of said Penning trap. Ions of same mass and same mass-to-charge ratio M/Z are then rotating at their cyclotron frequency, as a "packet" of ions, and generate a measurable electric signal. The Fourier transform of this electric signal gives access to a mass spectrum. FTICR mass spectrometry is a high resolution technique but is limited to the detection of particles having a mass less than or equal to $10^6$ Da, due to the required amplitude of the magnetic field needed to trap the particles.

The second technique is based on TOF ("Time-Of-Flight") mass spectrometry, in which an ion's mass-to-charge ratio M/Z is determined via a time measurement. Ions are accelerated by an electric field of known strength. After this acceleration, all ions of same charge have the same kinetic energy, The velocity of the ions depends on their mass-to-charge ratio M/Z. The time that it takes for the ions to reach a detector at a known distance is measured. Mass-to-charge ratios M/Z of ions are obtained from this time and the known experimental parameters. The ions are however destructed when detected: ion detection indeed involves bombarding the ion on a semi-conductor surface, causing the removing of electrons of said surface. The signal associated to the removed electrons is amplified for example with an electron multiplier, and an observable signal is thus generated for each ion bombarding the surface. Removing electron(s) from the semi-conductor surface also implies a minimal impulsion for the ions; said minimal impulsion can be given to ions having a mass less than $10^6$ Da.

A high resolution mass spectrometry method and system for analysis of whole proteins and other large molecules is described in patent US 2008/0230692 A1. This document aims in particular at providing an injection method of ions inside an ion trap, in order to extend the working mass range of an ion trap mass spectrometer and thus to allow real-time analysis of large molecules having a mass over 20 kDa. The proposed injection method is based on a MALDI ("Matrix-Assisted Laser Desorption Ionization") technique. Document US 2008/0230692 A1 then uses TOF mass spectrometry: ions are fragmented by collision with a high-temperature surface, fragments are then ionized by electron impact ionization, and ionized fragments are finally detected with a classic electron multiplier. The proposed method is thus destructive for the detected ions. Electron impact ionization is further highly dependent of the nature of the fragments, inducing that the efficiency of the detection is not constant according to the ions to be detected. The proposed method is therefore inappropriate for quantitative and comparative measurements of two different types of ions.

In this context, there is a need for a method allowing ion detection without mass limitation. There is also a need for a method allowing non-destructive ion detection without mass limitation. There is also a need for a method allowing non-destructive single ion detection without mass limitation. There is also a need for a method allowing non-destructive single ion detection without mass limitation and independently of the nature of the ion.

SUMMARY

The present invention addresses the technical problems identified above. An objective of the invention is to provide a non-destructive method for detecting charged particles comprising the steps of:
  measuring a reference value of at least one physical parameter of an ion cloud confined in an ion trap;
  performing an injection of a sample in the ion cloud confined in the ion trap, the sample crossing the ion cloud and getting out the ion cloud without being trapped inside the ion trap;
  measuring a first experimental value of the at least one physical parameter of the ion cloud;
  comparing the first experimental value with the reference value in order to determine the presence of at least one charged particle in the sample, or the absence of any charged particle in the sample.

In the present document, the expression "detecting charged particles" means "determining the presence of at least one charged particle, or the absence of any charged particle". In the present document, a charged particle, also referred to as "ion", is a particle having at least one charge. A charged particle may have more than one charge, but it is not necessary.

Thanks to an aspect of the invention, a sample to be tested is injected in an ion cloud, the ion cloud being confined in an ion trap. The said ion cloud is composed of atomic ions. The sample to be tested gets inside the ion cloud, crosses the ion cloud and gets out the ion cloud. The sample to be tested is not trapped inside the ion trap. The ion cloud remains confined in the ion trap. In the case where the sample comprises at least one charged particle, said injection of the sample in the ion cloud induces a perturbation of at least one physical parameter of the ion cloud. In the case where the sample does not comprise any charged particle, said at least one physical parameter of the ion cloud remains substantially unperturbed by the injection of the sample in the ion cloud. A reference value and an experimental value of said at least one physical parameter of the ion cloud are measured. Comparing the experimental value with the reference value then allows determining the presence of at least one charged particle in the sample, or the absence of any charged particle in the sample. A charged particle, also referred to as an external charged particle, is a particle that has been injected into the ion cloud for the purpose of detection. An external charged particle can be of any type. For example, an external charged particle can be an atom or a virus. An external charged particle is not trapped in the ion cloud. In contrast to that, the atomic ions of the ion cloud are trapped. The atomic ions of the ion cloud are typically simple singly-ionized atoms, which can be easily excited by a laser.

The method for detecting charged particles according to an aspect of the invention is beneficially non-destructive. The presence of at least one charged particle or the absence of any charged particle is indeed indirectly determined, using the ion cloud properties. The sample to be tested is therefore not destructed and can be reused. In the case where the sample comprises at least one charged particle, said at least one charged particle may be detected using the method according to an aspect of the invention without destroying said at least one charged particle, which can therefore be reused for other experiments.

The method for detecting charged particles according to an aspect of the invention is beneficially without mass limitation for the charged particles to be detected. In other words, the method according to an aspect of the invention has neither an upper nor a lower limit in mass range for the charged particles to be detected. Indeed the method according to an aspect of the invention does not require that the sample be trapped nor fragmented. The method according to an aspect of the invention is particularly adapted to the detection of ultra-massive charged particles, typically having a mass greater than $10^6$ Da. Indeed, the more massive is a charged particle, the slower it may move and the more it may perturb the ion cloud. However, every charged particle that crosses the ion cloud induces a measurable perturbation of the ion cloud and may thus be detected, independently of the mass of said charged particle. The method according to an aspect on the invention thus beneficially allows the detection of a single charged particle.

Apart from the characteristics mentioned above in the previous paragraph, the process of detection of light according to an aspect of the invention may have one or several complementary characteristics among the following characteristics considered individually or in any technically possible combinations:

The at least one physical parameter of the ions cloud is beneficially the fluorescence of the ion cloud. Indeed, it is an objective to precisely measure a temperature variation of the ion cloud, without interfering with said variation. A measurement of the fluorescence of the ion cloud does not modify the temperature of the ion cloud.

The step of measuring a first experimental value of at least one physical parameter of the ion cloud is beneficially performed after the sample crossed the ion cloud and came out of the ion cloud. Indeed, in the case where the crossing of the sample through the ion cloud induces a modification of the at least one physical parameter of the ion cloud, said modification is beneficially persistent. In other words, the ion cloud will keep the modified value of its at least one physical parameter at least over a significant duration and will not return automatically and immediately to the initial value of its at least one physical parameter. The expression "over a significant duration" means that the ion cloud keeps the modified value of its at least one physical parameter over a duration that is sufficient for said at least one physical parameter to be measured.

The step of measuring a first experimental value of at least one physical parameter of the ion cloud is performed during the crossing of the sample through the ion cloud and after the sample came out of the ion cloud.

The step of measuring a reference value of the at least one physical parameter of the ion cloud is performed before the injection of the sample in the ion cloud. The step of measuring a reference value of the at least one physical parameter of the ion cloud is thus performed before any perturbation of said at least one physical parameter of the ion cloud may have occurred.

The non-destructive method for detecting charged particles further comprises the step of analysing the first experimental value of the at least one physical parameter of the ion cloud in order to:
  determine the presence of at least one charged particle in the sample, or the absence of any charged particle in the sample, and
  in the case where the presence of at least one charged particle has been detected, determine the number of charge of said at least one charged particle.

The non-destructive method for detecting charged particles further comprises the steps of:
  guiding back the sample that came out of the ion cloud toward the ion cloud;
  performing a second injection of the sample in the ion cloud confined in the ion trap, the sample crossing the ion cloud and getting out the ion cloud without being trapped inside the ion trap;
  measuring a second experimental value of the at least one physical parameter of the ion cloud;
  comparing the first and second experimental values with the reference value in order to determine the presence of at least one charged particle in the sample, or the absence of any charged particle in the sample.

The ion cloud has:
  a first temperature before the sample is injected in the ion cloud, and
  a second temperature after the sample crossed the ion cloud and came out of the ion cloud;
  the second temperature being substantially equal to the first temperature when the sample comprises no charged particle, and the second temperature being greater than the first temperature when the sample comprises at least one charged particle.

Before the step of performing an injection of a sample in the ion cloud confined in the ion trap, the ion cloud has a temperature less than 100 K.

Other features and advantages of the invention will become apparent on examining the detailed specifications hereafter and the appended drawings.

DETAILED DESCRIPTION OF THE PREFERRED EMBODIMENT

Some embodiments of apparatus and methods in accordance with embodiments of the present invention are now described, by way of example only, and with reference to the accompanying drawings. The description is to be regarded as illustrative in nature and not as restricted.

Figure 1:
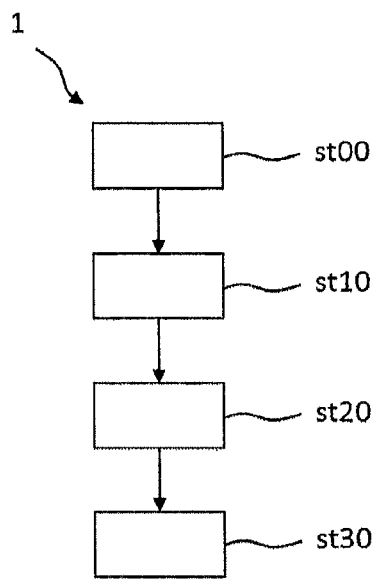
FIG. 1 schematically illustrates a method for detecting charged particles according to a first embodiment of the invention.

FIG. 1 schematically illustrates a method 1 for detecting charged particles according to a first embodiment of the invention.

The method 1 according to the first embodiment of the invention comprises:
- a step st00 of measuring a reference value of at least one physical parameter of an ion cloud confined in an ion trap;
- a step st10 of performing an injection of a sample in the ion cloud confined in the ion trap, the sample crossing the ion cloud and getting out the ion cloud without being trapped inside the ion trap;
- a step st20 of measuring an experimental value of the at least one physical parameter of the ion cloud;
- a step st30 of comparing the experimental value with the reference value in order to determine the presence of at least one charged particle in the sample, or the absence of any charged particle in the sample.

The ions of the ion cloud are also referred to as "ions" or "detection ions". The detection ions typically are singly-charged, atomic ions. The detection ions are excited by laser light fulfilling a resonance condition, that is to say, laser light at a wavelength matching an atomic transition of the detection ions. The detection ions may typically be magnesium ions or calcium ions.

For example:
singly-charged magnesium ions of mass M=28 Da and charge Z=+1 e have a charge-to-mass ratio M/Z=28 Da/e, and
singly-charged calcium ions of mass M=40 Da and charge Z=+1 e have a charge-to-mass ratio M/Z=40 Da/e,
with 1 Da≈$1.660 \times 10^{-27}$ kg and e≈$1.602 \times 10^{-19}$ C.

The ion cloud may typically comprise between 500 and 1000 detection ions. The dimensions of the ion cloud are typically of the order of one millimeter. The ion cloud dynamics is controlled by confinement potential, Coulomb repulsion between the ions of the cloud, and laser cooling. The confinement potential is typically of the order of a few hundred volts. The ion cloud is typically laser-cooled at a first temperature that is less than 100 K. The ion cloud may be laser cooled at a first temperature that is less than 1K. An only laser device is typically used both to excite the detection ions and to cool the ion cloud. The excitation of the detection ions may be realized permanently, in a continuous way, but it is not necessary. In such a case with permanent excitation of the detection ions and with an only laser device, experimental parameters of said laser device, such as power and frequency shift, are chosen in order to keep the detection ions cool. Said experimental parameters of the laser device are also chosen so that the cooling of the detection ions is not too strong and a perturbation of the ion cloud induced by a sample is easily detected. The trapping parameters of the ion trap are chosen according to the detection ions to be trapped. Indeed the trapping parameters are dependent on the charge-to-mass ratio M/Z of the detection ions. In other words, the ion trap is selective in charge-to-mass ratio M/Z and the choice of the experimental trapping parameters can be optimized so that a first species of detection ions is trapped while a second species of external charged particles is not trapped.

A stable confinement in an ion trap is determined by the frequency $\Omega/2\pi$ and the amplitude V_rf of the alternating radiofrequency trapping voltage that is applied, and by the amplitude of the static trapping voltage U_dc—in the case where a static trapping voltage is applied. A stable confinement in an ion trap is also determined by the spatial dimensions of the ion trap and by the charge-to-mass ratio M/Z of the ions to trap. In the case where both the detection ions and the external charged particle to be detected have the same charge-to-mass ratio M/Z, the kinetic energy of the charged particle to be detected is then chosen to be larger than the depth of the confinement potential well. In this way, the first species of detection ions may remain trapped while the second species of external charged particles remains untrapped.

Before the step st00 of measuring a reference value of the at least one physical parameter of the ion cloud, said ion cloud is laser cooled at a first temperature, and is in a first state referred to as "first equilibrium state". According to a particular example, the first temperature of the ion cloud is of the order of 10 mK.

The step st00 of measuring a reference value of at least one physical parameter of the ion cloud is performed before the step st10 of performing an injection of a sample in the ion cloud. The reference value is thus characteristic of the first equilibrium state.

The step st10 of performing an injection of a sample in the ion cloud may induce a perturbation of the first equilibrium state, resulting in the ion cloud passing in a second equilibrium state. In order to perform an injection of a sample in the ion cloud, various known injection methods may be used. It is for example possible to inject a sample in the ion cloud using an injection lens. It is also possible to inject a sample in the ion cloud using deflectors and a short flight tube. It is also possible to inject a sample in the ion cloud using a focusing tube lens and an octopole ion guide. These examples are illustrative and not limiting. After the step st10, that is to say after the sample was injected in the ion cloud, crossed the ion cloud and came out of the ion cloud, the ion cloud has a second temperature.

In the case where the sample does not comprise any charged particle, the first equilibrium state is substantially unperturbed by the injection of the sample and the ion cloud remains in the first equilibrium state. As a consequence, the second temperature is substantially equal to the first temperature.

In the case where the sample comprises at least one charged particle, the first equilibrium state is perturbed by the injection of the sample and the ion cloud passes in the second equilibrium state. As a consequence, the second temperature is substantially greater than the first temperature: there is typically a factor 10 between the first temperature and the second temperature. In the case where the first temperature of the ion cloud is of the order of 10 mK, the second temperature of the ion cloud is thus of the order of at least 100 mK.

It is an objective to precisely measure the perturbation, that is to say the temperature variation, without interfering with said perturbation. In other words, the measurement of the perturbation does not modify the perturbation. The measurement of the temperature variation of the ion cloud thus enables to determine the presence of at least one charged particle in the sample, or the absence of any charged particle in the sample.

The perturbation, that is to say the temperature variation, causes a modification of the fluorescence signal of the ion cloud. It is to be noted that said temperature variation of the ion cloud is persistent, and thus that said modification of the fluorescence signal of the ion cloud is persistent. In other words, the ion cloud will keep the second temperature at least over a significant duration and will not return automatically and immediately to the first temperature. In the present document, the expression "over a significant duration" means that the ion cloud keeps the second temperature over a duration that is sufficient for the fluorescence signal associated to said temperature to be measured. A significant duration may thus be of the order of 1 millisecond. A measurement of the fluorescence of the ion cloud does not modify the temperature of the ion cloud.

The at least one physical parameter of the ion cloud of which a reference value and an experimental value are measured is therefore beneficially the fluorescence intensity, also referred to as "fluorescence signal", of the ion cloud. The method 1 for detecting charged particles according to the first embodiment of the invention therefore beneficially comprises a step st20 of measuring an experimental value of the fluorescence intensity of the ion cloud. The experimental value of the fluorescence intensity of the ion cloud is typically measured using a fluorescence detector, such as a photon counter. Alternatively, the at least one physical parameter of the ion cloud of which a reference value and an experimental value are measured may be the electronic excitation frequency of the ion cloud.

In typical experimental conditions, a single detection ion may emit a fluorescence signal comprising around $10^7$ photons per second, that is to say $10^4$ photons per millisecond. Considering an ion cloud comprising 1000 detection ions, said ion cloud may thus emit a fluorescence signal comprising around $10^7$ photons per millisecond. The fluorescence detector may have an efficiency of around $10^{-3}$, taking for example into account the solid angle, the gain, the transmission and the absorption of the optics of said fluorescence detector. It is thus possible to detect a signal comprising around $10^4$ photons per millisecond, from the signal emitted by the ion cloud and that comprises around $10^7$ photons per millisecond. For a good detection reliability, the perturbation of the at least one physical parameter of the ion cloud due to the crossing of a sample comprising at least one charged particle is superior to the statistical fluctuations of the reference signal, that is measured before the injection of the sample in the ion cloud, and of the experimental signal, that is measured after the sample crossed the ion cloud and came out of the ion cloud. In other words, the signal-to-noise ratio between the reference signal and the experimental signal is larger than the statistical fluctuations of the reference signal and of the experimental signal. Statistical fluctuations of a signal depend on the amplitude of said signal: in the example of a signal comprising N photons, statistical fluctuations, or "noise", of said signal is square root of N: $\sqrt{N}$.

In the case where the sample does not comprise any charged particle, the experimental signal, or experimental value, is typically substantially equal to the reference signal, or reference value. That is to say, the experimental signal is equal to the reference signal, with an error comprised within the statistical fluctuations of the reference signal. In the case where the sample comprises at least one charged particle, the experimental signal, or experimental value is substantially different from the reference signal, or reference value. In the preferred case where the at least one physical parameter of the ion cloud is the fluorescence of the ion cloud, the experimental value is substantially less than the reference value. The experimental value is typically less than or equal to 50% of the reference value. More precisely, the experimental value is typically less than or equal to 25% of the reference value.

Figure 2:
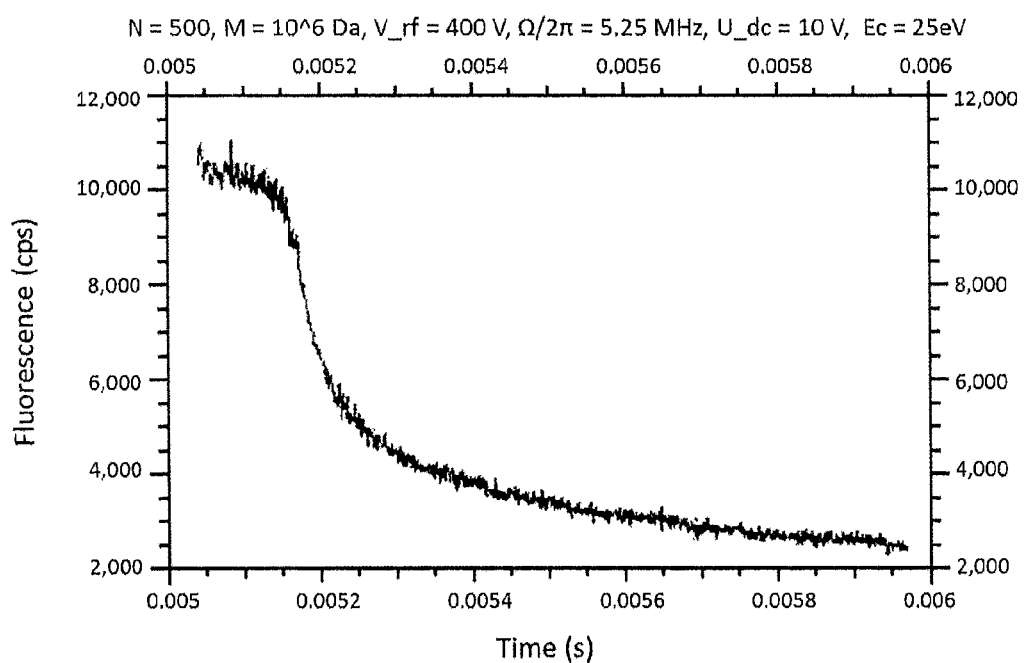
FIG. 2 schematically illustrates a diagram of the modification of the fluorescence signal of an ion cloud confined in an ion trap, induced by a sample injected in the ion cloud, according to the first embodiment of the invention.

FIG. 2 schematically illustrates a diagram of the modification of the fluorescence signal of the ion cloud, induced by a sample injected in the ion cloud, the sample then crossing the ion cloud and getting out the ion cloud without being trapped inside the ion trap. The fluorescence signal is measured in counts per second cps. The experimental parameters of the particular example of FIG. 2 are the following:
 the ion cloud comprises N=500 ions;
 the sample comprises a single charged particle, the charged particle having a mass $M=10^6$ Da;
 the amplitude of the alternating radiofrequency trapping voltage is: V_rf =400 V;
 the frequency of the alternating radiofrequency trapping voltage is: $\Omega/2\pi$=5.25 MHz;
 the amplitude of the static trapping voltage is: U_dc=10 V;
 the sample has an incident energy Ec=25 eV;
 the fluorescence detector has an efficiency of $10^{-3}$.

The incident energy of the sample is determined and controlled during a creation process of said sample, and then during a guiding process of said sample. The guiding process of the sample typically enables to slow down or to accelerate the sample. The creation process of the sample may for example use an electrospray ionization ESI technique, as described later. The guiding process of the sample may for example use electric fields of known strength.

FIG. 2 shows that the modification of the fluorescence signal of the ion cloud may be observed over a time scale of the order of 1 millisecond. On the particular example of FIG. 2, the fluorescence signal taken 5 milliseconds after the beginning of the recording is around 10,000 cps, and the fluorescence signal taken 6 milliseconds after the beginning of the recording is around 2,000 cps. FIG. 2 therefore shows a decrease from around 10,000 cps to around 2,000 cps, that is to say a 80% decrease, over a time scale of the order of 1 millisecond.

The step st00 of measuring a reference value of the at least one physical parameter of the ion cloud is performed before the injection of the sample in the ion cloud, that is to say before any perturbation of the ion cloud may occur.

The step st20 of measuring an experimental value of at least one physical parameter of the ion cloud is performed after the sample crossed the ion cloud and came out of the ion cloud, that is to say after any perturbation of the ion cloud may have occurred. An experimental value of the at least one physical parameter of the ion cloud may be measured only after the sample came out of the ion cloud, and not during the time when the sample is injected in the ion cloud, crosses the ion cloud and gets out of the ion cloud, because of the persistence of the second temperature of the ion cloud, previously described.

Alternatively, the step st20 of measuring an experimental value of at least one physical parameter is performed during the crossing of the sample through the ion cloud and after the sample came out of the ion cloud.

The step st00 of measuring a reference value and the step st20 of measuring an experimental value may be performed in a single action, that is to say for example by performing a single continuous recording of the at least one physical parameter of the ion cloud, between a first moment occurring before the injection of the sample in the ion cloud and a second moment occurring after the sample came out of the ion cloud. Alternatively, the step st00 of measuring a reference value and the step st20 of measuring an experimental value may be performed in at least two distinct actions, that is to say for example by performing:
- a first measurement of the at least one physical parameter of the ion cloud at a first moment occurring before the injection of the sample in the ion cloud, and
- a second measurement of the at least one physical parameter of the ion cloud at a second moment occurring:
  - after the sample came out of the ion cloud,
  - or alternatively, during the crossing of the sample through the ion cloud and after the sample came out of the ion cloud.

The first measurement may be a first recording occurring for a first duration comprising the first moment defined above. The second measurement may be a second recording occurring for a second duration comprising the second moment defined above. In the case where the first measurement is a first recording and the second measurement is a second recording, the first recording and the second recording beneficially do not overlap.

In the particular example described in relation with FIG. 2, the fluorescence signal of the ion cloud may beneficially be recorded during the entire experiment, that is to say:
- before the injection of the sample in the ion cloud, for example for a duration of the order of 1 millisecond,
- during the time when the sample is injected in the ion cloud, crosses the ion cloud and gets out of the ion cloud, and
- after the sample came out of the ion cloud, typically for a duration of the order of 1 millisecond, that is to say more generally for a duration allowing the fluorescence detector to measure a fluorescence signal that is sufficient to determine in a reliable way the presence of at least one charged particle in the sample, or the absence of any charged particle in the sample.

Figure 3:
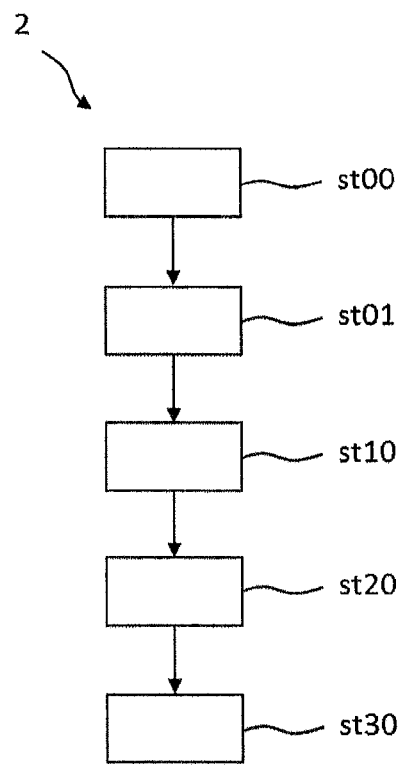
FIG. 3 schematically illustrates a method for detecting charged particles according to a second embodiment of the invention.

FIG. 3 schematically illustrates a method 2 for detecting charged particles according to a second embodiment of the invention.

The method 2 according to the second embodiment of the invention comprises:
- the step st00, previously described, of measuring a reference value of the at least one physical parameter of the ion cloud;
- a step st01 of ionizing a sample;
- the step st10, previously described, of performing an injection of the sample in the ion cloud confined in the ion trap, the sample crossing the ion cloud and getting out the ion cloud without being trapped inside the ion trap;
- the step st20, previously described, of measuring an experimental value of the at least one physical parameter of the ion cloud;
- the step st30, previously described, of comparing the experimental value with the reference value in order to determine the presence of at least one charged particle in the sample, or the absence of any charged particle in the sample.

Before the step st01 of ionizing the sample, the sample may comprise at least one uncharged particle. After the step st01 of ionizing the sample, the sample does not comprise any uncharged particle. In other words:
- in a first case, the sample initially comprises at least one particle, either charged or uncharged. In said first case, after the step st01 of ionizing the sample, every particle of the sample is charged;
- in a second case, the sample is empty and does not comprise any particle.

In said second case, the step st01 of ionizing the sample has no effect.

The step st01 of ionizing the sample may be performed using an electrospray ionization ESI technique. The electrospray ionization ESI technique creates charged particles in a highly charged state, which is not necessary for the method according to an embodiment of the invention. Indeed the method for detecting charged particles according to an embodiment of the invention allows the detection of charged particles in a low charged state, that is to say of charged particles having at least one charge.

Alternatively, the step st01 of ionizing the sample may beneficially be performed using a MALDI ("Matrix-Assisted Laser Desorption/Ionization") technique. Indeed the MALDI technique produces ions having far fewer multiple charges than the ESI technique.

During the non-destructive method for detecting charged particles according to any of the embodiments of the invention, neither the sample nor the ion cloud are destructed.

After getting out of the ion trap, the sample typically continues its trajectory. The sample may typically be slowed down by its crossing through the ion cloud. The sample may be reused for other experiments, and in particular for the non-destructive method for detecting charged particles according to an embodiment of the invention.

As previously described, before being crossed by the sample, the ion cloud is laser cooled at a first temperature. After being crossed by the sample, the ion cloud has a second temperature that may typically be larger than the first temperature. Indeed, the crossing of the ion cloud by a sample comprising at least one charged particle induces a warming of the ion cloud. In that case, the temperature of the ion cloud may be brought back to its initial value, that is to say to the first temperature, by modifying the parameters of the cooling laser. The ion cloud may be reused for other experiments, and in particular for the non-destructive method for detecting charged particles according to an embodiment of the invention.

The method for detecting charged particles according to an embodiment of the invention may further comprise a step of characterizing and/or identifying charged particles. The step of characterizing and/or identifying charged particles may for example use a time-of-flight TOF technique. If said step of characterizing and/or identifying charged particles is non-destructive, it may be performed before or after the steps for detecting charged particles according to an embodiment of the invention. If said step of characterizing and/or identifying charged particles is destructive, it is performed after the steps for detecting charged particles according to an embodiment of the invention.

Figure 4:
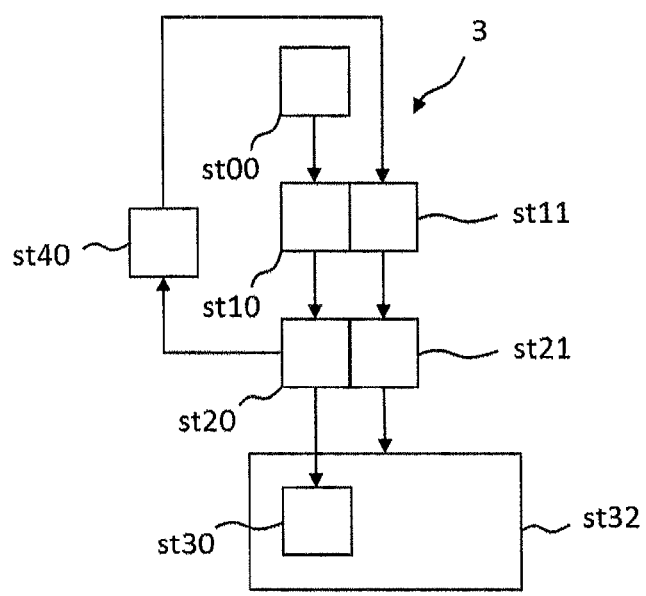
FIG. 4 schematically illustrates a method for detecting charged particles according to a third embodiment of the invention.

FIG. 4 schematically illustrates a method 3 for detecting charged particles according to a third embodiment of the invention.

The method 3 according to the third embodiment of the invention comprises: the step st00 of measuring a reference value of at least one physical parameter of an ion cloud confined in an ion trap;

the step st10 of performing an injection of a sample in the ion cloud confined in the ion trap, the sample crossing the ion cloud and getting out the ion cloud without being trapped inside the ion trap;

the step st20 of measuring a first experimental value of the at least one physical parameter of the ion cloud;

4a step st40 of guiding back the sample that came out of the ion cloud toward the ion cloud;

a step st11 of performing a second injection of the sample in the ion cloud confined in the ion trap, the sample crossing the ion cloud and getting out the ion cloud without being trapped inside the ion trap;

a step st21 of measuring a second experimental value of the at least one physical parameter of the ion cloud;

a step st32 of comparing the first and second experimental values with the reference value in order to determine the presence of at least one charged particle in the sample, or the absence of any charged particle in the sample.

Thanks to the method 3 according to the third embodiment of the invention, the sample is injected twice in the ion cloud and two experimental values of the at least one physical parameter of the ion cloud are measured. The determination of the presence of at least one charged particle in the sample, or of the absence of any charged particle in the sample, may thus use the comparison of two experimental values, instead of one, with the reference value. The first experimental value and the second experimental value may for example be averaged, and the average value of the first and second experimental values be compared with the reference value. The reliability of the determination may thus be improved. After the step st21 of measuring the second experimental value of the at least one physical parameter of the ion cloud, it is of course possible to:

guide again the sample that came out of the ion cloud toward the ion cloud;

perform a third injection of the sample in the ion cloud confined in the ion trap, the sample crossing the ion cloud and getting out the ion cloud without being trapped inside the ion trap;

measure a third experimental value of the at least one physical parameter of the ion cloud;

compare the first, second and third experimental values with the reference value in order to determine the presence of at least one charged particle in the sample, or the absence of any charged particle in the sample.

According to a variation, the method 3 may further comprise a step st01 of ionizing a sample. Said variation thus combines the method 2 according to the second embodiment of the invention, previously described, with the method 3 according to the third embodiment of the invention. For example, the step st01 of ionizing a sample is performed after the step st00 of measuring a reference value and before the step st10 of performing an injection of the sample in the ion cloud.

The invention claimed is:

1. A non-destructive method for detecting charged particles comprising:
   measuring a reference value of at least one physical parameter of an ion cloud confined in an ion trap;
   performing an injection of a sample in the ion cloud confined in the ion trap, the sample crossing the ion cloud and getting out the ion cloud without being trapped inside the ion trap;
   measuring a first experimental value of the at least one physical parameter of the ion cloud;
   comparing the first experimental value with the reference value in order to determine a presence of at least one charged particle in the sample, or an absence of any charged particle in the sample.

2. A non-destructive method for detecting charged particles according to claim 1, wherein the at least one physical parameter of the ions cloud is a fluorescence of the ion cloud.

3. A non-destructive method for detecting charged particles according to claim 1, wherein measuring a first experimental value of at least one physical parameter of the ion cloud is performed after the sample crossed the ion cloud and came out of the ion cloud.

4. A non-destructive method for detecting charged particles according to claim 1, wherein measuring a first experimental value of at least one physical parameter of the ion cloud is performed during the crossing of the sample through the ion cloud and after the sample came out of the ion cloud.

5. A non-destructive method for detecting charged particles according to claim 1, wherein measuring a reference value of the at least one physical parameter of the ion cloud is performed before the injection of the sample in the ion cloud.

6. A non-destructive method for detecting charged particles according to claim 1, further comprising analysing the first experimental value of the at least one physical parameter of the ion cloud in order to:
   determine the presence of at least one charged particle in the sample, or the absence of any charged particle in the sample, and
   in the case where the presence of at least one charged particle has been detected, determine the number of charges of said at least one charged particle.

7. A non-destructive method for detecting charged particles according to claim 1, further comprising:
   guiding back the sample that came out of the ion cloud toward the ion cloud;
   performing a second injection of the sample in the ion cloud confined in the ion trap, the sample crossing the ion cloud and getting out the ion cloud without being trapped inside the ion trap;
   measuring a second experimental value of the at least one physical parameter of the ion cloud;
   comparing the first and second experimental values with the reference value in order to determine the presence of at least one charged particle in the sample, or the absence of any charged particle in the sample.

8. A non-destructive method for detecting charged particles according to claim 1, wherein the ion cloud has:
   a first temperature before the sample is injected in the ion cloud, and
   a second temperature after the sample crossed the ion cloud and came out of the ion cloud;
   the second temperature being substantially equal to the first temperature when the sample comprises no charged particle, and the second temperature being greater than the first temperature when the sample comprises at least one charged particle.

9. A non-destructive method for detecting charged particles according to claim 1, wherein, before performing an injection of a sample in the ion cloud confined in the ion trap, the ion cloud has a temperature less than 100 K.

* * * * *